United States Patent [19]

Scherfel

[11] 4,261,351

[45] Apr. 14, 1981

[54] MEDULLARY CAVITY PIN

[75] Inventor: Tibor Scherfel, Debrecen, Hungary

[73] Assignee: Novex Talalmanyfejlesztöes ErtekesitöKülkereskedelmi Rt., Budapest, Hungary

[21] Appl. No.: 75,813

[22] Filed: Sep. 14, 1979

[51] Int. Cl.³ .......................... A61F 5/04; A61B 17/18
[52] U.S. Cl. ............................................... 128/92 BC
[58] Field of Search ......... 128/92 BC, 92 BB, 92 BA, 128/92 B, 92 R

[56] References Cited

U.S. PATENT DOCUMENTS 3,783,860  1/1974  Burnstein et al. ............... 128/92 BC

FOREIGN PATENT DOCUMENTS 913228  6/1954  Fed. Rep. of Germany ...... 128/92 BC
2109162  5/1972  Fed. Rep. of Germany ...... 128/92 BC
2361933  1/1976  Fed. Rep. of Germany ...... 128/92 BC
196245  11/1967  U.S.S.R. ............................. 128/92 BA

OTHER PUBLICATIONS

"Modified Küntscher's Nail for the Proximal Femur Fixation After Corrective Osteotomies in Children", by I. Ruszkowski et al., Arch. Orthop. Unfall Chir., 1977, pp. 240–244.

Intradmedullary Nails–Küntscher Nails, Zimmer Product Encyclopedia, Zimmer-USA, Box 768, Warsaw, Indiana, Jun. 1978, pp. B53–B56.

*Primary Examiner*—Ronald L. Frinks

[57] ABSTRACT

The invention relates to a therapeutic aid suitable for the stabilization of limb bone fractures with surgery. Minimum three radially arranged reinforcing lamellae are extending from the pin shank, the width of which is decreasing from the pin head in the direction of the pin point. The longitudinal dimension reduction of the lamellae is sectional, but continuous within each section. Number of the lamella sections is minimum two, while at junction of the adjacent lamella sections recessed steps are developed toward the longitudinal axis of the pin.

The medullary cavity pin according to the invention is applicable with very good result in case of femoral fractures below the buttock, because it is well adaptable to the varying cross section of the medullary cavity, it does not damage the bone, it gives sufficient stability, while the surgery is fast and simple.

7 Claims, 4 Drawing Figures

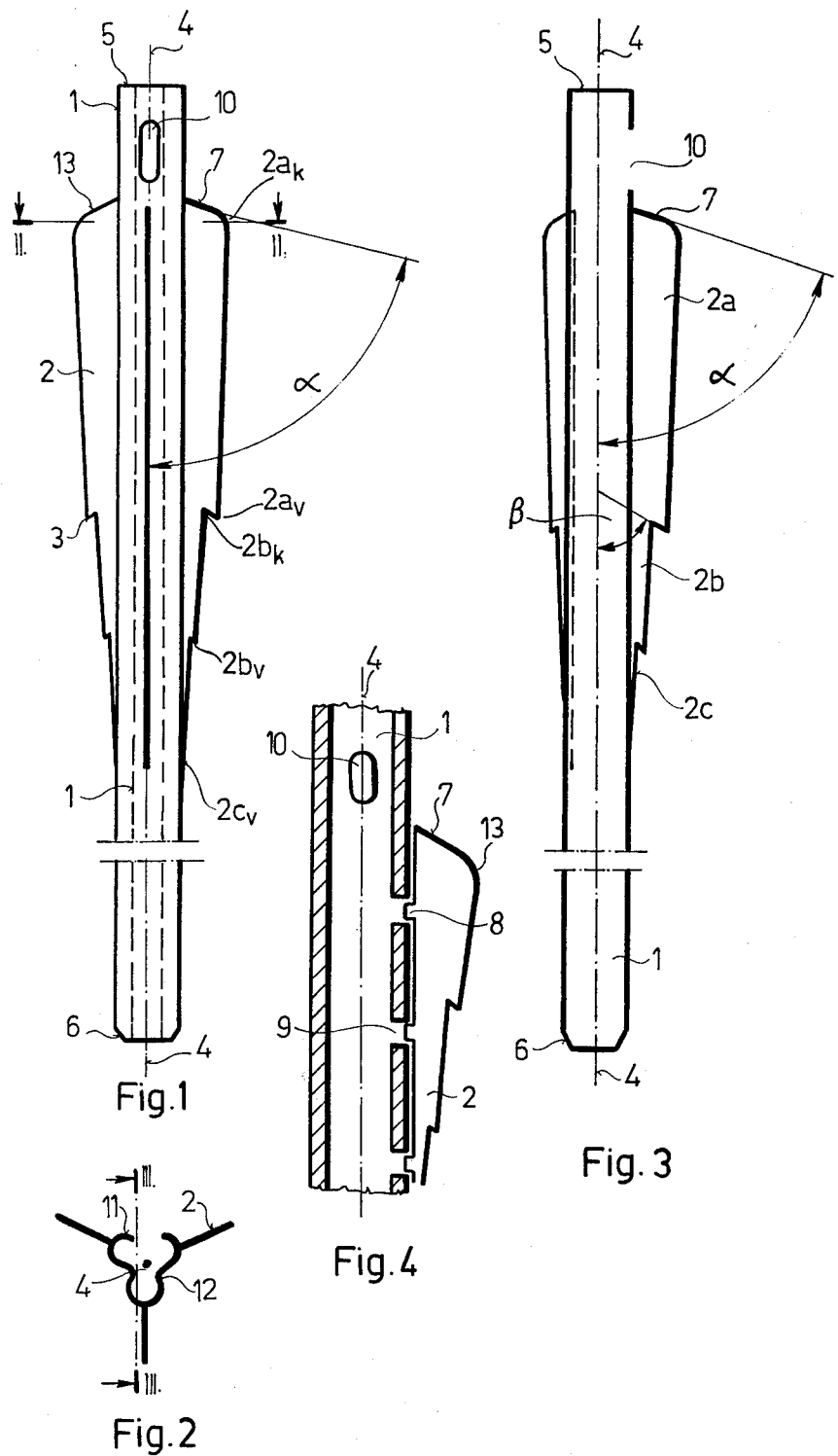

MEDULLARY CAVITY PIN

The invention relates to a medullary cavity pin for therapeutic purposes to stabilize the fractures of tubular limb bone, mainly subtrochanteric fractures of the femur by surgery, which pin has a shank introducable into the medullary cavity of the fractured bone. One end of the shank is tapered to facilitate the insertion, while the other end is shaped to be suitable for taking up the force that brings about the insertion. Its cross section is enlarged in relation to the shank and having a suitable formation to facilitate the withdrawal, e.g. a head part provided with orifice. Cross section of the pin shank between the head part and tapered end is approximately constant and it is circular or polygonal with rounded corners. In the latter case the edges parallel with the longitudinal axis of the pin are shaped as rounded reinforcing border ribs and channels between the border ribs are running in the longitudinal direction of the shank. Blade-like reinforcing lamellae are running similarly in longitudinal direction along the shank of the pin with decreasing cross section as moving away from the pin head.

Those cases when the tubular cross sectional bone of an injured person's limb breaks, come under the human medical science and within it come the delicate cases of casualty surgery. The healing of these bone fractures is slow and it is affected to a great extent upon how successful is the joining of the fractured surfaces, as well as their fastening to each other after the joining and during the process of healing.

According to experience a relatively short healing period can be achieved only if the relative displacement of the fractured parts can be effectively prevented. The Küntscher-type pin has been used for several decades for this purpose, which can be driven into the medullary cavity of the fractured bone resulting in sufficiently stable immobilization.

The Küntscher-type medullary cavity pin was initially used even by its originator only at fractures of the femur. His method was subsequently further developed partly by himself and partly by others. The so-called drilled Küntscher nailing method is where the medullary cavity is drilled, suitably with flexible drill—and a pin corresponding to the size of the hole is driven into the medullary cavity. As a result of further minor modifications the medullary cavity pin became suitable for its application in cases of the transversal or slightly oblique fractures of the tibia.

The original idea was further developed again recently in Switzerland and accordingly a circular cross sectional medullary cavity pin was produced.

The common deficiency of the known medullary cavity pins is that up to the present the reliable stabilization of the fractured bones was not successfully realized in case of subtrochanteric fractures which occurred in the femur. This can be attributed to the fact that the medullary cavity of the femur is of varying cross section.

In view of the varying cross section of the medullary cavity such pins have been used up to now, the thickness of which was adjusted to the narrowest cross section of the medullary cavity. This part of the narrowest cross sectional medullary cavity is in the middle third of the femur. If such pin is used the thickness of which fits this cross section, then the pin does not fill in the upper and lower part of the medullary cavity, i.e. the part with larger cross section. It will "dangle" in it, hence it can not fulfill the required stabilization task.

If the traditional medullary cavity pins are used and their cross section exceeds the narrowest inside diameter of the medullary cavity, then it will exert an unfavourable stretching force and may even cause the longitudinal splitting of the femur.

In view of the mentioned difficulties the medullary cavity pin—otherwise having several advantages—could not be used in subtrochanteric fractures of the femur, but various fastenings were placed onto the external surface of the femur, e.g. femoral neck pins with long extension, femoral neck pins with fixed extension, pin plates, etc. However these too are unfavourable for several reasons, since partly very large surgical exposure had to be performed—practically the thigh of the patient was cut all along in longitudinal direction. On the other hand the surgery took a long time, while the results were not satisfactory and both the surgery and the post-operative period had debilitating effect on the patients.

The invention is aimed at the development of such medullary cavity pin which in contrast with the traditional medullary cavity pins is suitable for stabilization even in case of subtrochanteric fractures of the femur. It requires minor surgical exposure, while insertion of the pin is fast and simple.

The inventive idea is based on the recognition that in case of femurs, i.e. in case of bones with varying cross sectional medullary cavity, stabilization can be expected from the pin only if its cross section is adapted to the varying inside dimension of the medullary cavity, while the cross-section variation is shaped as to prevent further injury of the femur. According to the recognition the external mantle surface of the medullary cavity pin is provided with sectionally reducing cross sectional lamellae extending in longitudinal direction, which prevents "dangling" of the medullary cavity pin, as well as turning in the medullary cavity.

The invention comprises a medullary cavity pin for internal fixation of long bone fractures in the form of an elongated hollow tube open at each end and having a top end and a bottom end characterized in having, on the upper third of said tube, at least three radially arranged, longitudinally disposed, blade-like lamellae extending outwardly from the said tube, each lamella having at least an upper section which is wider and longer than an adjoining lower section, each section having a top edge which is wider than its bottom edge, the bottom edge of each section being wider than the top edge of the adjoining lower section to form a recessed step, and the top edge of the uppermost section of each lamella forms an acute angle with the longitudinal axis of the said tube.

The medullary cavity pin has one end which is tapered to facilitate insertion into the medullary cavity while the other end is shaped to be suitable for taking up the force that brings about the penetration. Its cross section is enlarged in relation to the shank and has a suitable formation to facilitate the withdrawal, e.g. has a head part provided with an Orifice. The cross section of the shank between the head part and the tapered end is approximately constant and it is circular or with rounded polygonal corners; In the latter case the edges parallel with the longitudinal axis of the pin are shaped as rounded reinforcing border ribs and channels run between the border ribs in longitudinal direction of the shank reinforcing lamellae are arranged running similarly in longitudinal direction along the shank of the pin with decreasing cross section moving away from the pin head. This is constructed to stabilize the fractures of the femur with surgery in such a way that the number of the reinforcing lamellae along the shank of the pin is at least three. The reinforcing lamellae are connected to the shank of the pin integrally or with a mechanical joint, e.g. fastened with the aid of extensions in the holes prepared in the shank of the pin. The reinforcing lamellae are radially arranged in the cross section perpendicular to the shank of the pin and reduction of the cross section in longitudinal direction is sectional but continuous within the sections. The shoulder of the largest cross sectional lamella section facing the head and nearest to the pin head is at an acute angle to the longitudinal axis of the pin. The number of the lamella sections is at minimum two, while at junction of the adjacent lamella sections, steps recessed toward the longitudinal axis of the pin are developed.

A further advantageous feature of the medullary cavity pin according to the invention is that at the steps separating the lamella sections the end point of the preceding lamella section nearest to the pin head is farther from the longitudinal axis of the pin than the starting point of the adjacent lamella section farther from the pin head.

Preferably the direction of the edges of the steps separating the adjacent lamella sections determined by the starting and end points of the adjacent lamella sections are at an acute angle to the longitudinal axis of the pin.

According to a further advantageous embodiment the angle of the shoulder of the largest lamella to the longitudinal axis of the pin is between 45° and 85°, preferably between 60° and 80°, while the corner of the shoulder farther from the longitudinal axis of the pin is rounded. The angle of the edges of the steps between the adjacent lamella sections to the longitudinal axis of the pin is between 40° and 80°, preferably between 50° and 70°.

At a further suitable embodiment of the medullary cavity pin according to the invention the reinforcing lamellae are fitted to the reinforcing ribs of the pin shank and their number preferably agrees with the number of the reinforcing ribs.

The medullary cavity pin according to the invention has several advantages in comparison with the earlier traditional constructions. The most important advantage is that it is well adapted to the varying cross section of the medullary cavity, does not damage the bone and ensures stability against the longitudinal, lateral and torsional displacements of the bone parts.

It is applicable even in case of multiple fracture and in case of spiral or flexural sphenoid fracture it can be readily and effectively combined with loops made of tissue-tolerant, stainless steel wire woven around the bone.

Furthermore the medullary cavity pin according to the invention is favourable because the forces reacting along the surface of the fracture are distributed on a large surface, thus bending of the metal, its breakage due to fatigue, or its break out of the bone can not occur. According to experience the lamellar medullary cavity pin with correctly selected dimensions safely withstands the external force of arbitrary direction.

The invention will be further described in detail by way of example only with reference to the accompanying drawings, in which:

FIG. 1 is a longitudinal view of the medullary cavity pin according to the invention, FIG. 2 is a cross section along the line II—II in FIG. 1, FIG. 3 is a longitudinal section along the line III—III in FIG. 2, FIG. 4 is a cross section of the connection of the reinforcing lamellae to the pin shank.

In FIG. 1 the middle section of the shank of a medullary cavity pin according to the invention is not shown, only the upper section provided with a reinforcing lamellae 2 and a tapered pin end 6. The reinforcing lamellae 2 themselves may consist of several sections.

In the case shown in FIG. 1 three sections are shown. The lamella section 2a nearest to the pin head 5 is the widest and longest; then moving away from the pin head 5 the second lamella section 2b is narrower; while the third lamella section 2c is the narrowest and the end of this latter one farther from the pin head 5 merges with the surface of the pin shank 1.

Width of all the three lamella sections 2a, 2b, 2c is decreasing as moving away from the pin head 5. Accordingly the end point $2a_v$ of the lamella section 2a is nearer to the longitudinal axis 4 of the pin than its starting point and similarly $2b_v$ is nearer to the longitudinal axis 4 than $2b_k$. The third lamella section 2c—in this example—does not stand out at all from the surface of the pin shank at the end point $2c_v$.

FIGS. 1 and 2 show that a recessed step 3 is developed at each junction of the lamella sections 2a, 2b, 2c, the outer point of which is the end point of the lamella section nearer to the pin head 5, while its inner point is the starting point of the lamella section—adjacent to the former one—farther from the pin head 5. Naturally the reinforcing lamellae 2 may consist of more than three sections and even the narrowest section may end in a recessed edge.

The end nearer to the pin head 5 of the lamella section 2a nearest to the pin head 5 is developed as a shoulder at an acute angle between $\alpha = 60°$ and $\alpha = 80°$ to the longitudinal axis 4 of the medullary cavity pin. At junctions of the lamella sections the steps 3 are at an angle between $\alpha = 50°$ and $\alpha = 70°$ to the longitudinal axis 4 of the medullary cavity pin.

FIG. 2 shows the cross section of the medullary cavity pin according to which in this example the pin shank 1 is provided with three reinforcing lamellae 2 standing out of it in radial direction. It is not necessary that the pin shank 1 should have a closed cross section returning into itself, but it may be bent from a flat shape too in such a way that its edges do not meet, and the cross section remains open. The pin shank 1 is a polygon with as many sides as the number of the required reinforcing lamellae 2, but it may be of circular cross section as well.

In the interest of the bending rigidity of the pin shank 1 it is advisable to develop the parts of the cross section at the reinforcing lamellae 2 as reinforcing ribs 11, between which channels 12 nearer to the longitudinal axis 4 of the medullary cavity pin are formed.

FIG. 4 illustrates a possible solution for joining the reinforcing lamellae 2 to the pin shank 1. Accordingly holes 9 are made in the pin shank along the reinforcing lamellae 2, while the edge of the reinforcing lamellae facing the pin shank 1 is provided with extensions 8 fitting into the holes 9. In addition to this mechanical connection the reinforcing lamellae 2 can be fixed to the pin shank 1 integrally, as by welding.

The medullary cavity pin according to the invention is applicable both as a pin remaining inside or to be recovered. In the latter case it is necessary to develop an orifice 10 in the vicinity of the pin head 5, or in case of circular cross sectional medullary cavity pin such internally threaded connection piece through which a withdrawing force can be applied. Similarly the withdrawal is facilitated if the outer corner 13 of the shoulder 7 of lamella section 2a nearest to the pin head 5 is rounded.

The medullary cavity pin according to the invention is highly suitable for the surgery of subtrochanteric fractures of the femur, because it gives a stability exceeding by far the possibilities existing up to now. It requires minor surgery and its introduction and removal are fast and simple. Owing to its formation, the fatigue breakage of the metal and its breaking out of the bone are avoidable.

What we claim is:

1. A medullary cavity pin for internal fixation of long bone fractures in the form of an elongated hollow tube open at each end and having a top end and a bottom end characterized in having, on the upper third of said tube, at least three radially arranged, longitudinally disposed, blade-like lamellae extending outwardly from the said tube, each lamella having at least an upper section which is wider and longer than an adjoining lower section, each section having a top edge which is wider than its bottom edge, the bottom edge of each section being wider than the top edge of the adjoining lower section to form a recessed step, and the top edge of the uppermost section of each lamella forms an acute angle with the longitudinal axis of the said tube.

2. A medullary pin as in claim 1 wherein the said top edge of the uppermost section of each lamella is rounded at the point furthest away from the longitudinal axis of the said tube.

3. A medullary pin as in claim 1 wherein a recessed area is present in the surface of the said tube between adjacent lamellae.

4. A medullary pin as in claim 1 wherein the top edge of every section forms an acute angle with the longitudinal axis of the said tube.

5. A medullary pin as in claim 1 wherein the said acute angle is between 45 and 85 degrees, and preferably between 60 and 80 degrees.

6. A medullary pin as in claim 4 wherein the acute angle is between 45 and 85 degrees, and preferably between 60 and 80 degrees.

7. A meduallary pin as in claim 1 wherein the top end of the said tube is provided with a hole in its surface for easy withdrawal from the medullary cavity.

* * * * *